United States Patent [19]

Bigge et al.

[11] Patent Number: 5,284,862
[45] Date of Patent: Feb. 8, 1994

[54] DERIVATIVES OF 2-CARBOXYINDOLES HAVING PHARMACEUTICAL ACTIVITY

[75] Inventors: Christopher F. Bigge; Graham Johnson; Po-Wai Yuen, all of Ann Arbor, Mich.

[73] Assignee: Warner-Lambert Company, Morris Plains, N.J.

[21] Appl. No.: 839,109

[22] Filed: Feb. 27, 1992

Related U.S. Application Data

[63] Continuation-in-part of Ser. No. 670,860, Mar. 18, 1991, abandoned.

[51] Int. Cl.$^5$ .............. C07D 209/18; C07D 405/12; C07D 409/12; A61K 31/405; A61K 31/38
[52] U.S. Cl. ..................... 514/419; 548/492
[58] Field of Search ............. 548/492; 514/419

[56] References Cited

U.S. PATENT DOCUMENTS

| 4,148,895 | 4/1979 | Lattrell et al. ............. 424/248.54 |
| 4,960,786 | 10/1990 | Salituro et al. ............... 514/419 |
| 5,137,910 | 4/1992 | Gray et al. .................... 514/419 |

FOREIGN PATENT DOCUMENTS

| 90107633 | 10/1990 | European Pat. Off. . |
| 90108337 | 11/1990 | European Pat. Off. . |
| 228962 | 9/1989 | Japan . |

OTHER PUBLICATIONS

R. Schwarcz et al., *The Lancet*, 140 (1985).
D. W. Choi, *Neuron*, 1:623 (1988).
B. Meldrun, "Neurotoxins and Their Pharmacological Implications", edited by P. Jenner, Raven Press, New York (1987).
J. W. McDonald et al., *Eur. J. Pharmocol.*, 140:359 (1987).
J. F. Church et al., *Anesthesiology*, 69:702 (1988).
R. Gill et al., *J. Neurosci.*, 7:3343 (1987).
S. M. Rothman et al., *Neurosci.*, 21:673 (1987).
M. P. Goldbert et al., *Neurosci. Lett.*, 80:11 (1987).
L. F. Copeland et al., *Soc. Neurosci. Abstr.*, 14 (part 1): 420 (1988).
J. A. Kemp et al., *TIPS*, 8:414 (1987).
R. Gill et al., *J. Neurosci.*, 25:847 (1988).
C. K. Park et al., *Ann. Neurol.*, 24:543 (1988).
G. K. Steinberg et al., *Stroke*, 19:1112 (1988).
PCT International Search Report for corresponding PCT Application PCT/US92/01699, Mar. 4, 1992.

*Primary Examiner*—David B. Springer
*Attorney, Agent, or Firm*—Ronald A. Daignault; Elizabeth M. Anderson

[57] ABSTRACT

The present invention relates to novel 3-substituted-2-carboxyindoles; including as 3-substituents amides of hydroxamic acids and derivatives thereof or urea and carbonyl, carboxyl or phosphonic acids or ester amides, or 2-acylsulfonamides thereof; and including also as 3-substituents unsaturated acids and their further ester and amide derivatives. These 2-carboxyindoles are useful as pharmaceutical agents, therefore, the present invention is also pharmaceutical compositions and pharmaceutical methods of treatment therefor. The compounds of the present invention are useful in the treatment of neurodegenerative disorders including cerebrovascular disorders.

14 Claims, No Drawings

DERIVATIVES OF 2-CARBOXYINDOLES HAVING PHARMACEUTICAL ACTIVITY

CROSS-REFERENCE TO RELATED APPLICATION

This is a continuation in-part of U.S. application Ser. No. 670,860 of Mar. 18, 1991, abandoned.

BACKGROUND OF THE INVENTION

The present invention relates to novel compounds, which are 3-acyl and acylamido derivatives; including derivatives of hydroxamic acids or amide derivatives of ureas, carbonyl esters, carboxy esters, or sulfones and esters thereof, of 2-carboxyindoles. The present invention also relates to novel compounds which are 2-carboxyindoles having an unsaturated carboxylic acid group and derivatives thereof at the 3 position. The novel compounds of the present invention are useful as pharmaceutical agents and, therefore, the present invention also relates to methods for the preparation of the compounds, to pharmaceutical compositions, and to methods of use therefor. More specifically, the compounds of the present invention are useful in the treatment of neurodegenerative disorders including cerebrovascular disorders as well as in the treatment of schizophrenia or epilepsy; and as analgesics and anxiolytics.

Excessive excitation by neurotransmitters can cause the degeneration and death of neurons. It is believed that this degeneration is in part mediated by the excitotoxic actions of the excitatory amino acids (EAA) glutamate and aspartate at N-methyl-D-aspartate (NMDA), α-amino-3-hydroxy-5-methyl-isoxazole propionic acid (AMPA), and kainate receptor. This excitotoxic action is responsible for the loss of neurons in cerebrovascular disorders such as cerebral ischemia or cerebral infarction resulting from a range of conditions, such as thromboembolic or hemorrhagic stroke, cerebral vasospasm, hypoglycemia, cardiac arrest, status epilepticus, perinatal asphyxia, anoxia such as from drowning, pulmonary surgery and cerebral trauma.

There are no specific therapies for these neurodegenerative diseases; however, compounds which act specifically as antagonists of EAA receptors and in particular the NMDA receptor complex, either competitively or noncompetitively, offer a novel therapeutic approach to these disorders: R. Schwarcz and B. Meldrum, *The Lancet* 140 (1985); B. Meldrum in "Neurotoxins and Their Pharmacological Implications" edited by P. Jenner, Raven Press, New York (1987); D. W. Choi, *Neuron* 1:623 (1988). Confirmation of the protective effects of noncompetitive NMDA antagonists in various pharmacological models of neurodegenerative disorders have appeared in the literature: J. W. McDonald, F. S. Silverstein, and M. V. Johnston, *Eur. J. Pharmacol.* 140:359 (1987); R. Gill, A. C. Foster, and G. N. Woodruff, *J. Neurosci.* 7:3343 (1987); S. M. Rothman, J. H. Thurston, R. E. Hauhart, G. D. Clark, and J. S. Soloman, *Neurosci.* 21:673 (1987); M. P. Goldbert, P-C. Pham, and D. W. Choi, *Neurosci. Lett.* 80:11 (1987); L. F. Copeland, P. A. Boxer, and F. W. Marcoux, *Soc. Neurosci. Abstr.* 14 (part 1):420 (1988); J. A. Kemp, A. C. Foster, R. Gill, and G. N. Woodruff, *TIPS* 8:414 (1987); R. Gill, A. C. Foster, and G. N. Woodruff *J. Neurosci.* 25:847 (1988); C. K. Park, D. G. Nehls, D. I. Graham, G. M. Teasdale, and J. M. McCulloch, *Ann. Neurol.* 24:543 (1988); G. K. Steinburg, C. P. George, R. DeLaPlaz, D. K. Shibata, and T. Gross, *Stroke* 19:1112 (1988); J. F. Church, S. Zeman, and D. Lodge, *Anesthesiology* 69:702 (1988).

U.S. Pat. No. 4,960,736 discloses certain 2-carboxylic indole derivatives useful as excitatory (EAA) amino acid antagonists and EP Application Numbers 90107633.1 and 90108337.8 also disclose certain 2-carboxylic indole derivatives for use to treat neurotoxic injury or neurodegenerative diseases known to be caused by or accelerated by certain EAAs found in the central nervous system (CNS).

Each of these references differs from the present invention by the hydroxamide, amide, urea amide, ester amide or sulfonamide substituent on an acyl group of the 2-carboxyindoles as disclosed herein. Also not taught by these references is the use of unsaturated acids and derivatives thereof, for example, hydroxamide, amide, urea amide, ester amide, or sulfonamide products such as now found in the present invention. Therefore, each of the aforementioned publications differs from the present invention.

SUMMARY OF THE INVENTION

The present invention provides compounds of the formula (I or II)

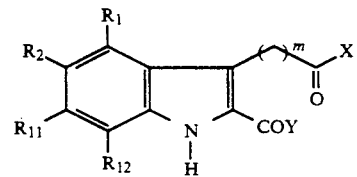

or

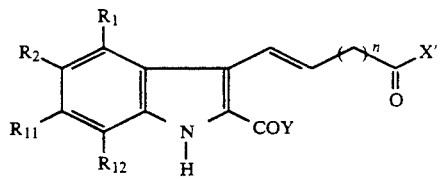

or a pharmaceutically acceptable base or acid addition salt thereof; wherein m is an integer of one to three; and n is an integer of zero or one;

(1) Y is OH; $OR_{30}$ wherein $R_{30}$ is lower alkyl, optionally substituted phenyl, or phenylalkyl wherein the alkyl is an alkylenyl of from one to four carbons and the phenyl is optionally substituted; $NR_{40}R_{50}$ wherein $R_{40}$ and $R_{50}$ are independently hydrogen or lower alkyl; or $OCH_2OR_{30}$ wherein $R_{30}$ is as defined above;

(2) $R_1$, $R_2$, $R_{11}$, and $R_{12}$ are independently hydrogen, lower alkyl, halogen, trifluoromethyl, cyano, nitro, methylthio, lower alkenyl, lower alkynyl, $SO_2NH_2$, $S(O)_{1-2}R$ wherein R is hydrogen or lower alkyl, $OCF_3$, or two of $R_1$, $R_2$, $R_{11}$, and $R_{12}$ can be taken together to form a carbocyclic ring of six carbons or can be taken together to form a heterocyclic ring wherein the heteroatoms are selected from oxygen, sulfur, or nitrogen, and wherein the carbon on the carbocyclic ring is optionally further substituted by one of $R_1$, $R_2$, $R_{11}$, or $R_{12}$;

(3)

X' is OH;

$OR^{30}$ wherein $R_{30}$ is lower alkyl; Ar which is phenyl optionally substituted by from one to three substituents independently selected from halogens, lower alkyl, lower alkoxy, $CF_3$, $OCF_3$, OH, CN, and $NO_2$; aralkyl wherein Ar is as defined above and alkyl is an alkylenyl of one to four carbons; or $OCH_2OR_5$ wherein $R_5$ is independently as defined below; or X wherein (4) X is
  (a) $NR^6SO_2R^{60}$,
  (b) $NR^6R^3$,
  (c) $NR^6OR^3$,
  (d) $NR^6CONR^3R^4$,
  (e) $NR^6COR^5$, or
  (f) $NR^6CO_2R^3$, wherein
  (I) $R^3$ and $R^4$ are independently
    (i) hydrogen; (ii) alkyl of from one to twenty carbons, preferably one to twelve carbons; (iii) cycloalkyl or cycloalkylloweralkyl; (iv) alkenyl of from two to twenty carbons, preferably two to twelve carbons; (v) alkynyl of from two to twenty carbons, preferably two to twelve carbons; (vi) aryl which is phenyl unsubstituted or substituted by one to three of lower alkyl, halogen, trifluoromethyl, nitro, amino, mono- or di-lower alkylamino, azido, hydroxy, lower alkoxy, C(O)OH, or $NHCOR^5$ wherein $R^5$ is independently as defined below, $NHSO_2R^5$ wherein $R^5$ is independently as defined herein, CN, $CONR^8R^6$ wherein $R^8$ and $R^6$ are independently as defined herein, $S(O)_{0-2}R$ wherein R is defined herein; (vii) aryl-loweralkyl; (viii) aryl-loweralkenyl; (ix) heterocycle; (x) heteroaryl; (xi) $(CH_2)_qR^7$ wherein q is an integer of one to four and $R^7$ is (A) heterocycle, (B) heteroaryl, (C) $SO_3R^8$ wherein $R^8$ is hydrogen or lower alkyl and R is independently as defined herein, (D) $PO_3R^8$ is as defined above, (E) $CO_2R^8$ wherein $R^8$ is as defined above, or (F) $NR^9R^{10}$ wherein $R^9$ and $R^{10}$ are independently hydrogen or alkyl or $R^9$ and $R^{10}$ are taken together with N to form a heterocyclic or heteroaryl ring; or (xii) amino acid residues;
  (II) $R^5$ is lower alkyl, lower alkenyl, aryl, aryloweralkyl, arylloweralkenyl, heteroaryl or heteroarylloweralkyl;
  (III) $R^6$ is hydrogen or lower alkyl, preferably hydrogen;
  (IV) $R^{60}$ is $R^3$ or

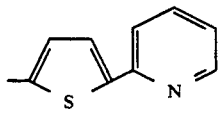

with the proviso that when X is in the compound of the formula I then X cannot be amino, monoalkylamino, or dialkylamino.

The present invention also includes a pharmaceutical composition comprising a therapeutically effective amount of a compound of Formula I together with a pharmaceutically acceptable carrier.

The present invention also includes a pharmaceutical composition for the use of treating cerebrovascular disorders, treating disorders responsive to the blockade of glutamic and aspartic acid receptors, or treating cerebral ischemia, cerebral infarction, cerebral vasospasm, hypoglycemia, cardiac arrest, status epilepticus, cerebral trauma, schizophrenia, epilepsy, neurodegenerative disorders, Alzheimer's disease, pain, anxiety, or Huntington's disease. Such a composition comprises an amount effective for treating such disorders together with a pharmaceutically acceptable carrier.

The present invention also includes a method of manufacturing a composition for or a method for treating cerebrovascular disorders which comprises administering to a patient in need thereof the above pharmaceutical composition in unit dosage form.

The present invention also includes a method of manufacturing a composition for or a method for treating disorders responsive to the blockade of glutamic and aspartic acid receptors comprising administering to a patient in need thereof a therapeutically effective amount of the above composition.

The invention also includes a method of manufacturing a composition for or a method for treating cerebral ischemia, cerebral infarction, cerebral vasospasm, hypoglycemia, cardiac arrest, status epilepticus, cerebral trauma, schizophrenia, epilepsy, neurodegenerative disorders, Alzheimer's disease, pain, anxiety, or Huntington's disease comprising administering to a patient in need thereof a therapeutically effective amount of the above composition.

The invention also includes a method of manufacturing a composition for or a method for treating stroke in patients in need thereof which comprises administering to a patient in need thereof a therapeutically effective amount of the above composition.

The invention further includes processes for the preparation of compounds of Formula I.

The invention still further includes novel intermediates useful in the processes.

Preferred compounds of the present invention are compounds of the Formula I wherein $R^1$ and $R^{11}$ are chloro, $R^2$ and $R^{12}$ are hydrogen, Y is OH, and X is $NHSO_2R^3$ or $NHR^3$ wherein $R^3$ is as defined above. Preferred compounds of the Formula II are the above wherein $X^1$ is OH, and X is $NHSO_2R^3$.

More preferred compounds of the present invention are compounds of the Formula I wherein $R^1$ and $R^{11}$ are chloro, $R^2$ and $R^{12}$ are hydrogen, Y is OH, and X is $NHS(O)_2CH_3$, $NHS(O)_2phenyl$, $NHS(O)_2(CH_2)_4H$ or NH phenyl or NH phenyl substituted by azido and are compounds of the Formula II wherein $R^1$ and $R^{11}$ are chloro, $R^2$ and $R^{12}$ are hydrogen, Y is OH, $X^1$ is OH, and X is $NHS(O)_2CH_3$, $NHS(O)_2phenyl$, NH phenyl, or $NHCH_2$ phenyl.

The most preferred compound of the instant invention is 4,6-dichloro-3-[3-oxo-3-[(phenylsulfonyl)amino]-1-propyl]-1H-indole-2-carboxylic acid.

DETAILED DESCRIPTION

The terms in the invention generally have the following meaning.

Loweralkyl means a straight chained or branched chain of from one to four carbon atoms including but not limited to methyl, ethyl, propyl, butyl.

Loweralkenyl means a group from two to four carbon atoms, for example, but not limited to ethylene, 1,2- or 2,3-propylene, 1,2- 2,3-, or 3,4-butylene.

Loweralkynyl means a group from two to four carbon atoms, for example, but not limited to ethynyl, 2,3-propynyl, 2,3-, or 3,4-butynyl; propynyl is the preferred group.

Cycloalkylloweralkyl means cycloalkyl of from three to six carbon atoms and lower alkyl as above, meaning for example, cyclopropylmethyl, cyclobutylmethyl, cyclopentylmethyl, cyclohexylmethyl, cyclopropylmethyl is the preferred group.

Loweralkoxy means a group of from one to four carbon atoms, for example, but not limited to methoxy, ethoxy, propoxy; methoxy is the preferred group.

Halogen is fluorine, chlorine, bromine, or iodine; fluorine, chlorine and bromine are the preferred groups.

Aryl means phenyl or phenyl substituted by one to three substituents defined above under $OR^{30}$ where $R^{30}$ is Ar or $R^3$ where $R^3$ is aryl.

Arylloweralkyl means aryl as defined above and alkyl as defined above, for example, benzyl, 2-phenylethyl, 3-phenylpropyl; preferred groups are benzyl and the benzyl or phenyl is as substituted above.

Arylloweralkenyl means aryl as defined above and alkenyl as defined above, for example, 2-phenylethenylenyl, 3-phenylpropenylenyl; preferred groups are 2-phenylethenylenyl and the phenyl is as substituted above.

Monoloweralkylamino means a group containing from one to four carbon atoms, for example, but not limited to methylamino, ethylamino, propylamino or butylamino and isomers thereof.

Diloweralkylamino means a group containing from one to four carbon atoms in each lower alkyl group, for example, but not limited to dimethylamino, diethylamino, di-(n-propyl)-amino, di-(n-butyl)-amino, or may represent a fused ring, for example piperidine.

Heteroaryl means a 5- or 6-membered monocyclic or fused bicyclic aromatic ring containing at least 1 to 4 heteroatoms in one ring if monocyclic or at least one of the ring if fused bicyclic, such as nitrogen, oxygen, or sulfur or a combination thereof, where possible. Such a heteroaryl group includes, for example, thienyl, benzothienyl, furanyl, benzofuranyl, pyridyl, pyrimidinyl, pyridazinyl, pyrazinyl, pyrrolyl, pyrazolyl, isothiazolyl, thiazolyl, oxazolyl, isoxazolyl, triazolyl, tetrazolyl, imidazolyl, thiadiazolyl, oxadiazolyl, benzothiazolyl, indolyl, quinolinyl, isoquinolinyl, or N oxides of heteroaryl containing a nitrogen atom.

More specifically, such a heteroaryl may be a 2- or 3-thienyl; 2- or 3-furanyl; 2-, or 3-, or 4-pyridyl or -pyridyl-N-oxide; 2-, 4-, or 5-pyrimidinyl; 3- or 4-pyridazinyl; 2-pyrazinyl; 2-pyrazinyl N-oxide; 2- or 3-pyrrolyl; 3-, 4-, or 5-pyrazolyl; 2-, 4-, or 5-oxazolyl; 2-, 4-, or 5-thiazolyl; 3-, 4-, or 5-isoxazolyl; 3-, 4-, or 5-isothiazolyl; 5-tetrazolyl; 3- or 5-(1,2,4,-)triazolyl; 4- or 5-(1,2,3-)triazolyl; 2-, 4-, or 5-imidazolyl; 2-, 3-, 4-, 5-, 6-, or 7-indolyl; 2-, 3-, 4-, 5-, 6-, 7-, or 8-quinolinyl; 1-, 3-, 4-, 5-, 6-, 7-, or 8-isoquinolinyl; 2-, 4-, 5-, 6-, or 7-benzothiazolyl; 2-, 3-, 4-, 5-, 6-, or aryl, or 7-benzothienyl.

Heterocycle means, in this case, a 5- or 6-membered saturated ring containing 1 to 3 heteroatoms such as nitrogen, oxygen, or sulfur or a combination thereof. Such a group includes, for example, piperadinyl, tetrahydro-pyridinyl, tetrahydropyranyl, pyrrolidinyl, pyrazolidinyl, oxazolidinyl, tetrahydrofuranyl, tetrahydrothienyl, and the like.

Amino acid residues means residues of glycine, alanine, isoleucine, leucine, valine, serine, threonine, aspartic acid, glutamic acid, asparagine, glutamine, arginine, lysine, 5-hydroxylysine, cysteine and cystine, methionine, phenylalanine, tyrosine, tryptophan, histidine, proline, or 4-hydroxyproline.

Well known protecting groups and their introduction and removal may be used according to the skill in the art and are described, for example, in J. F. W. McOmie, *Protective Groups in Organic Chemistry*, Plenum Press, London, New York (1973), and T. W. Greene, *Protective Groups in Organic Synthesis*, Wiley, New York (1981).

The compounds of the present invention may contain asymmetric carbon atoms. The instant invention may also include the individual diastereomers and enantiomers, which may be prepared or isolated by methods known to those skilled in the art.

Selected compounds of the present invention can exist also as syn and anti forms and are also the present invention. Selected compounds can also exist as E and Z double bond isomers. Both forms are included in the present invention.

Any resulting racemate can be resolved into the optical antipodes by known methods, for example by separation of the diastereomeric salts thereof, with an optically active acid, and liberating the optically active amine compound by treatment with a base. Racemic compounds of the present invention can thus be resolved into their optical antipodes e.g., by fractional crystallization of d- or l-(tartarates, mandelates, or camphorsulfonate) salts.

Additional methods for resolving optical isomers, known to those skilled in the art may be used, for example those discussed by J. Jaques, A. Collet, and S. Wilen in *Enantiomers, Racemates, and Resolutions*, John Wiley and Sons, New York (1981).

Salts of the compounds of the invention are preferably pharmaceutically acceptable salts. The compounds of the invention are acids, acid derivatives, or when possible basic amines. The basic amines may be used to make acid addition salts of pharmaceutically acceptable weak inorganic or organic acids.

The selected compounds of the invention that are acids are also acids from which base salts may be prepared.

The compounds of the instant invention exhibit valuable pharmacological properties by selectively blocking the sensitive excitatory amino acid receptors in mammals. The compounds are thus useful for treating diseases responsive to excitatory amino acid blockade in mammals.

Such disorders include but are not limited to cerebral ischemia or cerebral infraction resulting from a range of conditions such as thromboembolic or hemorrhagic stroke, cerebral vasospasm, hypoglycemia, cardiac arrest, status epilepticus, perinatal asphyxia, anoxia such as from drowning, pulmonary surgery, and cerebral trauma. Other treatments are for schizophrenia, epilepsy, spasticity, neurodegenerative disorders such as Alzheimer's disease or Huntington's disease, Olivo-pontocerebellar atrophy, spinal cord injury, and poisoning by exogenous NMDA poisons (e.g., some forms of lathyrism). Further uses include uses as analgesics and anxiolytics.

The effects are demonstrable in in vitro tests or in vivo animal tests using mammals or tissues or enzyme preparations thereof, e.g., mice, rats, or monkeys. The compounds are administered to patients enterally or parenterally, for example, orally, transdermally, subcutaneously, intravenously, or intraperitoneally. Forms include but are not limited to gelatin capsules, or aqueous suspensions or solutions. The applied in vivo dosage may range between about 0.01 to 100 mg/kg, preferably between about 0.05 and 50 mg/kg, most preferably between about 0.1 and 10 mg/kg.

BIOLOGICAL TESTING

Specifically, the compounds of the present invention have activity as antagonists at the strychnine insensitive glycine receptor which is located on the NMDA receptor complex. As such, the compounds of the present invention are NMDA receptor antagonists. Also, the compounds of the present invention have activity as AMPA and kainate receptor antagonists.

For example, compounds of the invention exhibit valuable biological properties because of these excitatory amino acid antagonizing properties. These properties may be ascertained in one or more of the following assays.

The glycine binding assay is performed essentially as described by W. Frost White, et al, *Journal of Neurochemistry* 1989;53(2):503–12.

The glutamate-induced lactate dehydrogenase (LDH) efflux assay is also used to measure the activity of the compounds of the present invention. Procedures for evaluating neurotoxicity in cortical neuronal cells by measuring efflux of LDH are carried out similarly as described by J. Y. Koh and D. W. Choi, *J. Neurosci. Methods* 1987;20:83–90. Only mature (50 to 20 days in vitro) cortical cultures were selected for study. Cells were exposed for 5 minutes to a glutamate exposure solution. Compounds tested were added to the glutamate exposure medium. In all experiments the glutamate exposure was removed and fresh buffer was added. Overall neuronal injury was quantitatively assessed by measurement of LDH released into the culture medium 1 day after glutamate exposure (see J. G. Klingman, D. M. Hartley, D. W. Choi, *J. Neurosci. Methods* 1989;31:47–51) using a 96-well plate reader.

The AMPA binding assay may also be performed to provide an activity profile for the compounds of the present invention.

The kainate binding assay is performed as described by T. Honore et al, *Neuroscience Letters* 1986;65:47–52.

Several compounds of the present invention have been tested in the above assays and the results of their activity are shown in the following table.

| Structure | [³H]-Gly (μM) | [³H]-AMPA (μM) | LDH (μM) |
|---|---|---|---|
| 4,6-dichloroindole-2-COOH with 3-(CH=CH-COOH) | 0.18 | 203 | 10.2 |
| 4,6-dichloroindole-2-COOH with 3-(CH₂CH₂C(O)NHSO₂Ph) | 0.068 | 113 | 7.8 |
| 4,6-dichloroindole-2-COOH with 3-(CH₂CH₂C(O)NHSO₂Me) | 0.543 | 80 | 21.5 |
| 4,6-dichloroindole-2-COOH with 3-(CH₂CH₂CH₂C(O)NHSO₂Ph) | 89% Inh. at 10 μM | 108 | — |
| 4,6-dichloroindole-2-COOH with 3-(CH₂CH₂C(O)NHSO₂-(3-N₃-phenyl)) | 0.079 | 150 | 6 |
| 4,6-dichloroindole-2-COOH with 3-(CH=CH-C(O)NHSO₂Ph) | 87% Inh. at 10 μM | 122 | — |

-continued

| Structure | [³H]-Gly (μM) | [³H]-AMPA (μM) | LDH (μM) |
|---|---|---|---|
| (4,7-dichloroindole-2-COOH with 3-CH=CH-CONH-CH₂-Ph) | 84% Inh. at 10 μM | 213 | — |

Therefore, the compounds of Formula I and of Formula II and their pharmacologically acceptable salts are effective agents in the prophylaxis and/or therapeutic treatment of disorders responsive to agents which block NMDA receptors, thus forming a further aspect of the present invention in like manner.

Methods of synthesis of the compounds of the instant invention are illustrated in Schemes A, B, and C. The preparation of compounds of the Formula I' wherein X is $NR^6SO_2R^3$, $NR^6R^3$, $NR^6OR^3$, $NR^6COR^5$, or $NR^6CO_2R^3$, X' is H, $OR_{30}$ or X; and $R_{11}$, $R_{12}$, and $R_1$, $R_2$, $R^3$, $R^4$, $R^5$, and $R^6$ are as previously defined and are illustrated in Schemes A, B, and C.

Further, preparation of compounds of the Formula I wherein X is $NHCONR^3R^4$ and $R^3$ is H and $R_1$, $R_2$, $R_{11}$, $R_{12}$, and $R^4$ are as previously defined are illustrated in Scheme B.

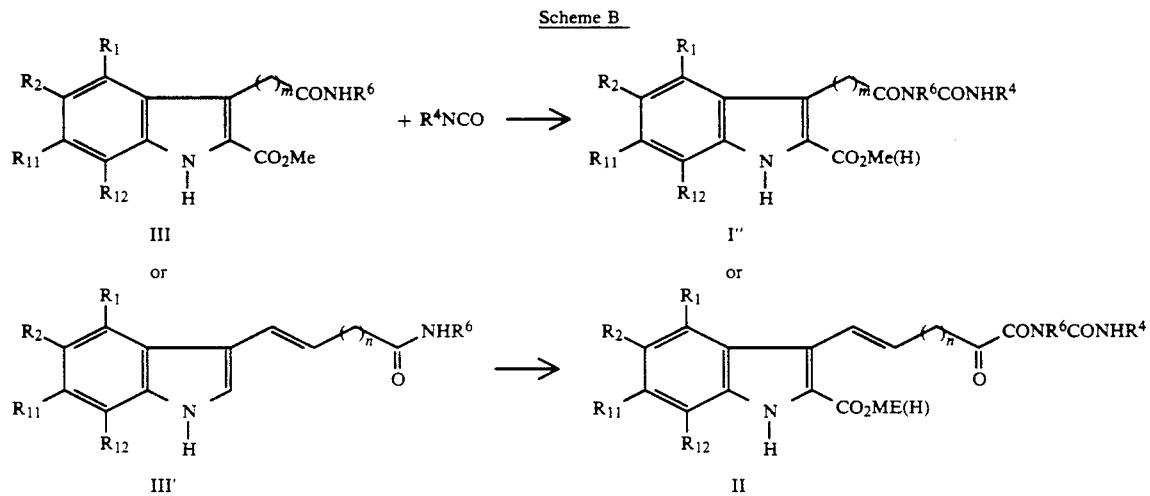

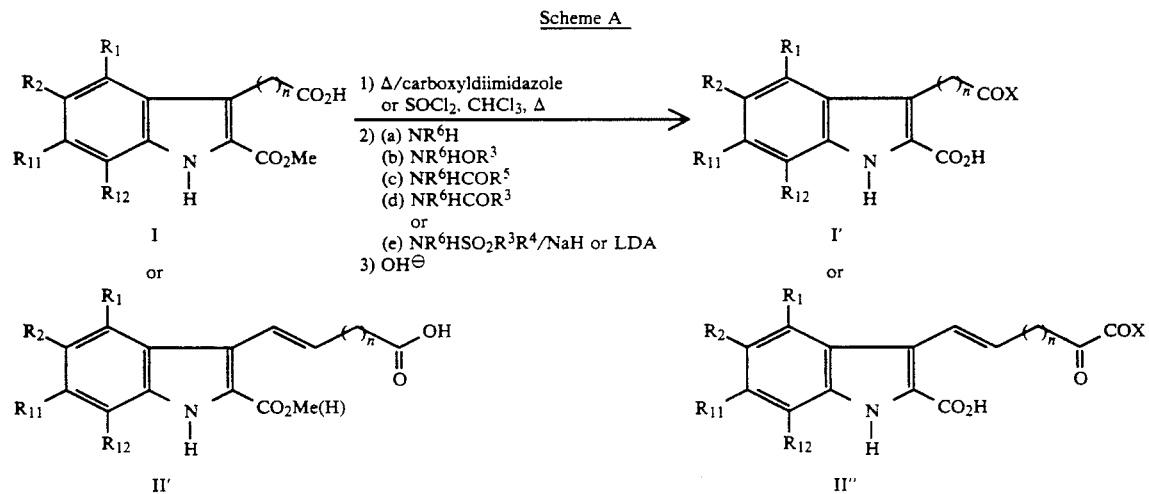

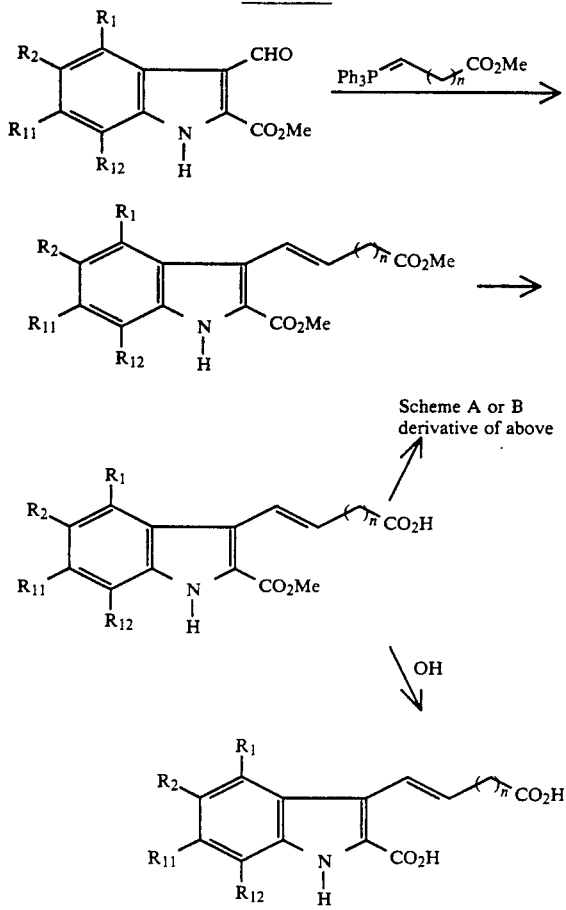

Generally, the compounds of the Formula I above wherein X is $NHSO_2R^3$, $NR^6R^3$, $NR^6OR^3$, $NR^6CONR^3R^4$, $NR^6COR^5$, and $NR^6CO_2R^3$ and where X' is OH, $OR^3$, or X wherein $R_1$, $R_2$, $R_{11}$, $R_{12}$, $R^3$, $R^4$, $R^5$, and $R^6$ are as defined above, are prepared by the method of Schemes A, B, and C above.

Scheme A consists of treating a carboxylic acid of the general structure I''' or II' with a coupling reagent in an inert solvent to produce an activated carboxylic acid derivative. The resulting activated carboxylic acid derivative is reacted with a variety of nitrogen nucleophiles to produce amides of the general structures I' or II', wherein X, $R^1$, $R^2$, $R^3$, $R^4$, $R^5$, and $R^6$ are as defined above. Suitable coupling agents for this purpose include, for example, such reagents as thionyl chloride, acetic anhydride, carbonyldiimidazole, DCC, and diphenylphosphoryl azide, preferably carbonyldiimidazole. By "activated carboxylic acid derivative" is meant an acid derivative which is capable of acylating an amine. Such acid derivatives include, for example, acid chlorides, acid bromides, anhydrides, and mixed anhydrides. By "inert solvent" is meant a nonprotic solvent such as, for example, methylene chloride, chloroform, carbon tetrachloride, ethyl acetate, tetrahydrofuran, and dimethylformamide.

The compounds of the Formula III or III' in Scheme B may optionally be reacted further to obtain compounds of the Formula I or II wherein X is $NR^6CONR^3R^4$ and $NR^6CO_2R^3$.

Overall the compounds prepared in the Schemes A, B, and C, steps 1) and 2) may optionally be further treated by conventional methods shown as step 3 in Scheme A to obtain compounds of the Formula I wherein Y is OH.

Pharmaceutically acceptable salts of the compounds of Formula I or II are also included as a part of the present invention.

The base salts may be generated from compounds of Formula I or II by reaction of the latter with one equivalent of a suitable nontoxic, pharmaceutically acceptable base followed by evaporation of the solvent employed for the reaction and recrystallization of the salt, if required. The compounds of Formula I may be recovered from the base salt by reaction of the salt with an aqueous solution of a suitable acid such as hydrobromic, hydrochloric, or acetic acid.

Suitable bases for forming base salts of the compounds of this invention include amines such as triethylamine or dibutylamine, or alkali metal bases and alkaline earth metal bases. Preferred alkali metal hydroxides and alkaline earth metal hydroxides as salt formers are the hydroxides of lithium, sodium, potassium, magnesium, or calcium. The class of bases suitable for the formation of nontoxic, pharmaceutically acceptable salts is well known to practitioners of the pharmaceutical formulation arts. See, for example, Stephen N. Berge, et al, *J. Pharm. Sci.* 1977;66:1-19.

Suitable acids for forming acid salts of the compounds of this invention containing a basic group include, but are not necessarily limited to acetic, benzoic, benzenesulfonic, tartaric, hydrobromic, hydrochloric, citric, fumaric, gluconic, glucuronic, glutamic, lactic, malic, maleic, methanesulfonic, pamoic, salicylic, stearic, succinic, sulfuric, and tartaric acids. The acid addition salts are formed by procedures well known in the art.

Further, the compounds of this invention may exist in unsolvated as well as solvated forms with pharmaceutically acceptable solvents such as water, ethanol and the like. In general, the solvated forms are considered equivalent to the unsolvated forms for the purposes of this invention.

Starting materials for the processes described above are known or can be prepared by known processes.

The products of the reactions described herein are isolated by conventional means such as extraction, distillation, chromatography, and the like.

Variations within the processes described are within the skill of the art for the preparation of compounds of the Formula I and II.

PHARMACEUTICAL COMPOSITIONS

The compounds of the present invention can be administered in a wide variety of oral and parenteral dosage forms. It will be obvious to those skilled in the art that the following dosage forms may comprise as the active component, either a compound of Formula I or a corresponding pharmaceutically acceptable salt of a compound of Formula I or Formula II.

For preparing pharmaceutical compositions from the compounds of the present invention, pharmaceutically acceptable carriers can be either solid or liquid. Solid form preparations include powders, tablets, pills, capsules, cachets, suppositories, and dispersible granules. A solid carrier can be one or more substances which may also act as diluents, flavoring agents, solubilizers, lubricants, suspending agents, binders, preservatives, tablet disintegrating agents, or an encapsulating material.

In powders, the carrier is a finely divided solid which is in a mixture with the finely divided active component.

In tablets, the active component is mixed with the carrier having the necessary binding properties in suitable proportions and compacted in the shape and size desired.

The powders and tablets preferably contain from five or ten to about seventy percent of the active compound. Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component, with or without carriers, is surrounded by a carrier, which is thus in association with it. Similarly, cachets and lozenges are included. Tablets, powders, capsules, pills, cachets, and lozenges can be used as solid dosage forms suitable for oral administration.

For preparing suppositories, a low melting wax, such as a mixture of fatty acid glycerides or cocoa butter, is first melted and the active component is dispersed homogeneously therein, as by stirring. The molten homogeneous mixture is then poured into convenient sized molds, allowed to cool, and thereby to solidify.

Liquid form preparations include solutions, suspensions, and emulsions, for example, water or water propylene glycol solutions. For example, parenteral injection liquid preparations can be formulated in solution in aqueous polyethylene glycol solution.

Aqueous solutions suitable for oral use can be prepared by dissolving the active component in water and adding suitable colorants, flavors, stabilizing and thickening agents, as desired.

Aqueous suspensions suitable for oral use can be made by dispersing the finely divided active component in water with viscous material, such as natural or synthetic gums, resins, methylcellulose, sodium carboxymethylcellulose, and other well-known suspending agents.

Also included are solid form preparations which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

The pharmaceutical preparation is preferably in unit dosage form. In such form, the preparation is subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg preferably 10 mg to 100 mg according to the particular application and the potency of the active component. The composition can, if desired, also contain other compatible therapeutic agents.

METHOD OF TREATING

The compounds of this invention are useful in the treatment of central nervous system disorders related to their biological activity. The compounds of this invention may accordingly be administered to a subject, including a human, in need of treatment, alleviation, or elimination of an indication associated with the biological activity of the compounds as set out above. This includes especially excitatory amino acid dependent psychosis, excitatory amino acid dependent anorexia, excitatory amino acid dependent ischemia, excitatory amino acid dependent convulsions, and excitatory amino acid dependent migraine. Suitable dosage ranges are 0.1 to 1000 mg daily, 10 to 400 mg daily, and especially 30 to 100 mg daily, dependent as usual upon the exact mode of administration, form in which administered, the indication toward which the administration is directed, the subject involved and the body weight of the subject involved, and further, the preference and experience of the physician in charge.

The following nonlimiting example illustrates the synthesis of a compound within the present invention. It is an indole acylsulfonamide having the formula 4 as outlined below.

Preparation of Selected Acylsulphonamides

The synthesis may be achieved by two slightly different routes shown below as either Scheme D or Scheme E.

The first route, shown in Scheme D below, involves the preparation of the indole-3-carboxaldehyde 1 from methyl 4,6-dichloro-2-indolecarboxylate by a Vilsmeier reaction. The side chain at 3-position of the indole 2 is incorporated by Wittig chemistry. Optional catalytic hydrogenation of the α,β-unsaturated ester 2 gives the indole carboxylic acid 3. The saturated acid 3 or unsaturated analog thereof is then converted to its acid chloride and is then reacted with lithium benzenesulfonamide to afford the acylsulfonamide 4 or the unsaturated analog thereof. Saponification of the methyl ester group of compound 4 or its unsaturated analog produces a compound which is of the formula 6.

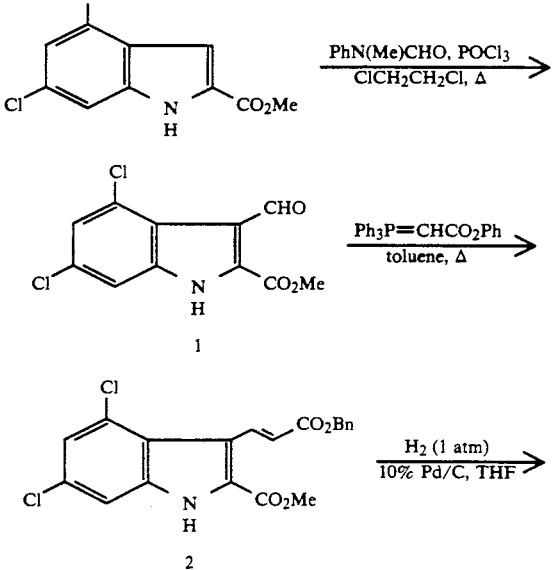

Scheme D

Scheme D -continued

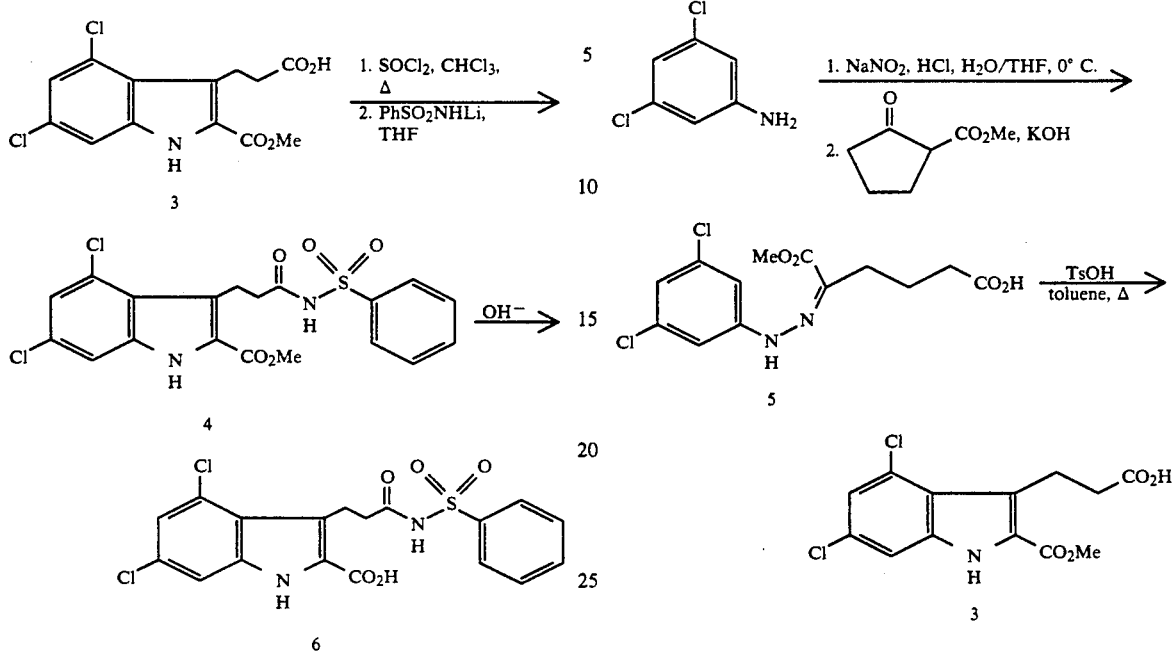

The indole carboxylic acid 3 may also be prepared by another route via Fischer indole synthesis from the corresponding hydrazone 5 as shown below in Scheme E.

Scheme E

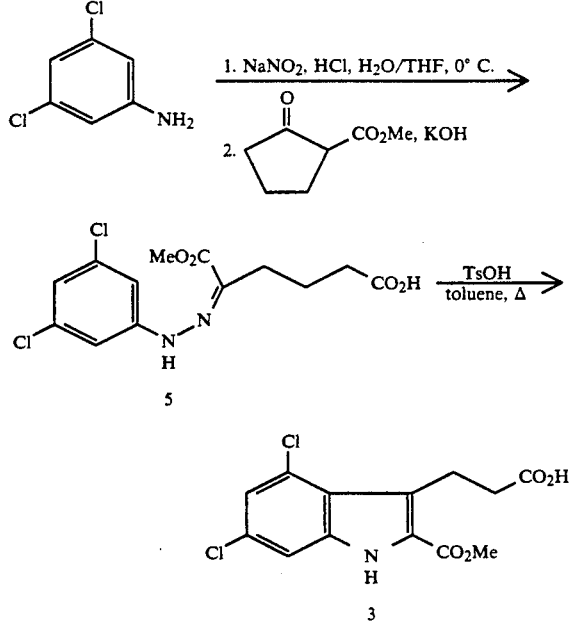

Scheme F below provides an alternative way to synthesize the above noted acylsulfonamide which is to couple indole-3-carboxaldehyde, such as aldehyde 1, with a Wittig reagent containing the required acylsulfonamide functionality, such as phosphorane 7. This methodology also provides the unsaturated analogs set out as Formula II above. Optional catalytic hydrogenation of compound 8 gives the desired acylsulfonamide 4. Alternate protecting group cleavage affords 2-carboxy products.

Scheme F

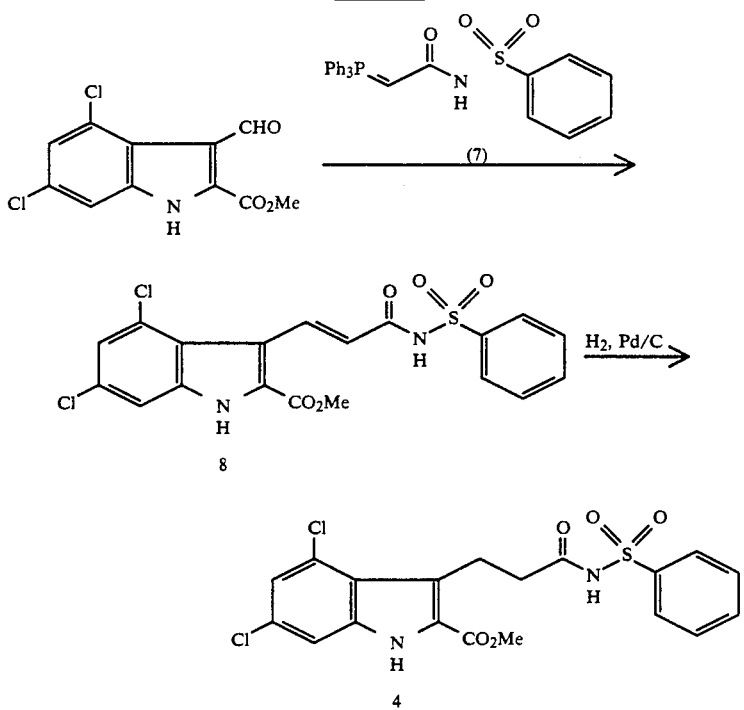

Scheme G shows the phosphorane 7 is synthesized by reaction of lithium benzenesulfonamide with α-bromoacetyl bromide followed by phosphonium salt is then converted to the phosphorane 7 by aqueous base treatment.

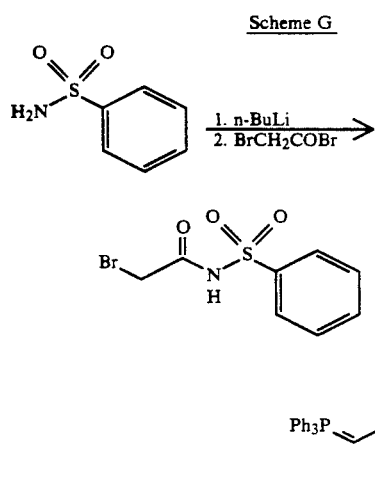

More specifically, the following preparations and examples illustrate the present invention.

PREPARATION 1

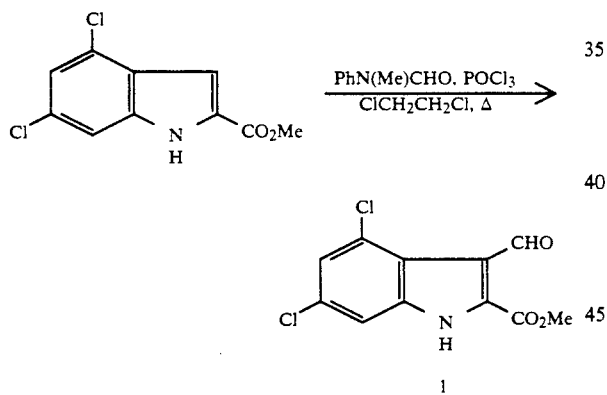

Ref: Shabica, A. C.; Howe, E. E.; Ziegler, J. B.; Tishler, M., *J. Am. Chem. Soc.*, 1946, 68, 1156.

A mixture of N-methylformanilide (7.85 g, 58.1 mmol) and phosphorus oxychloride (8.93 g, 58.2 mmol) is allowed to stir at room temperature for 15 minutes. Ethylene dichloride (40 mL) is added followed by methyl 4,6-dichloro 2-indolecarboxylate (12.04 g, 49.3 mmol). The reaction mixture is allowed to reflux for 2.5 hours and is then poured into a mixture containing sodium acetate (38 g) and ice-water mix (75 mL). The product separated is collected by filtration and washed with cold ether. The solid is then washed with water (3×) followed by cold ether (2×). The aldehyde 1 (8.85 g, 66%) was obtained after air-drying as an off-white solid; $^1$H NMR (DMSO-d$_6$, 200 MHz) δ 13.20 (br s, 1H), 10.62 (s, 1H), 7.55 (d, 1H, J=0.8Hz), 7.43 (d, 1H, J=0.8Hz), 3.98 (s, 3H).

PREPARATION 2

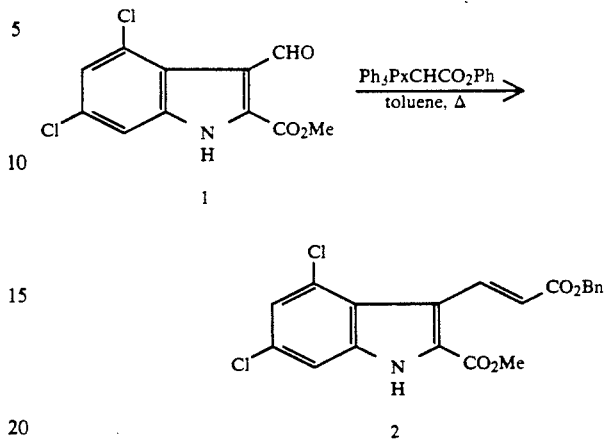

A suspension of the aldehyde 1 (4.85 g, 17.8 mmol) and benzyl(triphenylphosphoranylidene) acetate (9.60 g, 23.4 mmol) in 250 mL of toluene is allowed to reflux overnight. The reaction mixture is then concentrated and chromatographed by 30% ethyl acetate in hexanes on silica gel to give 6.58 g (91%) of the α,β-unsaturated ester 2 as a yellow solid: $^1$H NMR (DMSO-d$_6$, 200 MHz) δ 12.81 (s, 1H), 8.46 (d, 1H, J=16.53 Hz), 7.55-7.34 (m, 7H), 6.68 (d, 1H, J=16.53 Hz), 5.25 (s, 2H), 3.91 (s, 3H).

EXAMPLE 1

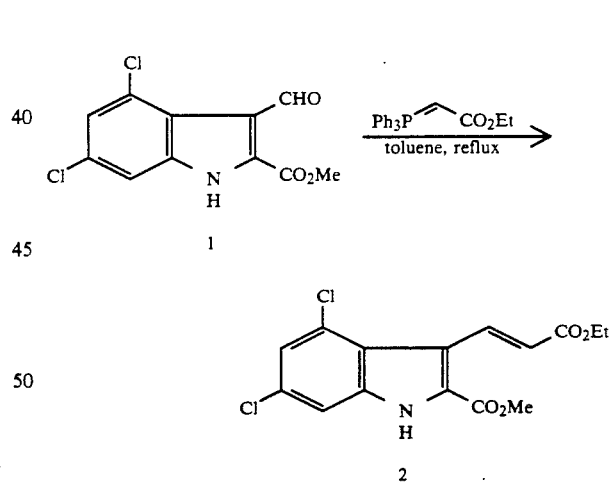

A suspension of the aldehyde 1 (4.0 g, 14.7 mmol) and ethyl (triphenylphosphranylidene)acetate (6.6 g, 18.9 mmol) in 250 mL of toluene is allowed to reflux overnight. The reaction mixture is then concentrated and chromatographed by 40% ethyl acetate in hexanes on silica gel to give 4.5 g (89%) of the α,β-unsaturated ester 2 as a yellow solid. $^1$H NMR (DMSO-d$_6$, 200 MHz) δ 12.79 (s, 1H), 8.39 (d, 1H, J=16.17 Hz), 7.51 (d, 1H, J=1.6 Hz), 7.34 (d, 1H, J=1.62 Hz), 6.60 (d, 1H, J=16.17 Hz), 4.21 (q, 2H, J=7.13 Hz), 3.92 (s, 3H), 1.27 (t, 3H, J=7.13 Hz).

EXAMPLE 2

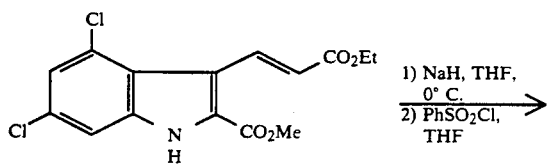

To a solution of the indole 2 (3.0 g, 8.77 mmol) in 50 mL anhydrous THF at 0° C. under argon atmosphere is slowly added a 60% dispersion of sodium hydride (0.6 g, 1.5 mmol) in mineral oil. The reaction mixture is allowed to stir at 0° C. for 15 minutes, then at room temperature for 30 minutes. Benzenesulfonyl chloride (1.3 mL, 10.2 mmol) is then added and the mixture was allowed to stir overnight at room temperature. The reaction mixture is then cooled to 0° C. and was quenched by the addition of saturated ammonium chloride solution followed by extractive workup with ethyl acetate (3×). The combined organics are dried with magnesium sulphate, filtered, and concentrated to give a yellow oil which is then chromatographed by 25% ethyl acetate in hexanes to give 3.24 g (77%) of the protected indole 3 as a pale yellow solid. $^1$H NMR (DMSO-d$_6$, 200 MHz) δ 8.10–7.65 (m, 8H), 6.16 (d, 1H, J=16.06 Hz), 4.20 (1, 2H, J=7.12 Hz), 3.97 (s, 3H), 1.25 (5, 3H, J=7.12 Hz).

EXAMPLE 3

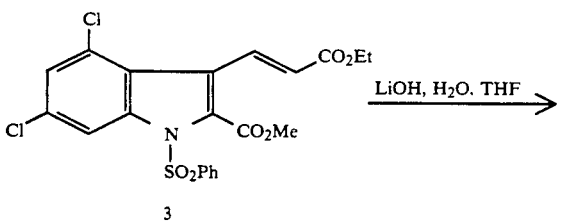

To a solution of the ester 3 (1.17 g, 2.42 mmol) in 6.5 mL of THF is added a 1M aqueous lithium hydroxide solution (11 mL, 11 mmol). The reaction mixture is allowed to stir at room temperature for 24 hours. Water (10 mL) is then added and the yellowish solution is cooled to 0° C. and acidified to pH 1 with concentrated hydrochloric acid. The precipitates are taken up by ethyl acetate containing a small amount of THF. The aqueous layer is extracted twice with ethyl acetate. The combined organic layers are dried with magnesium sulphate, filtered, and concentrated to give 0.55 g (76%) of the diacid 4 as a yellow solid. $^1$H NMR (DMSO-d$_6$, 200 MHz) δ 13.10 (brs, 2H), 12.64 (s, 1H), 8.35 (d, 1H, J=16.05 Hz), 7.50 (d, 1H, J=1.59 Hz), 7.32 (d, 1H, J=1.59 Hz), 6.52 (d, 1H, J=16.05 Hz).

PREPARATION 3

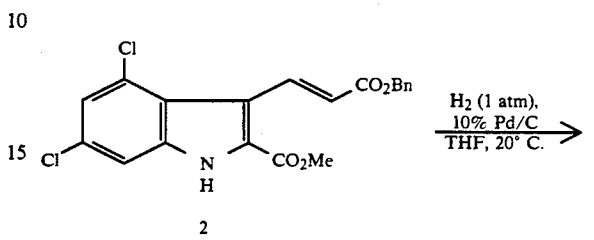

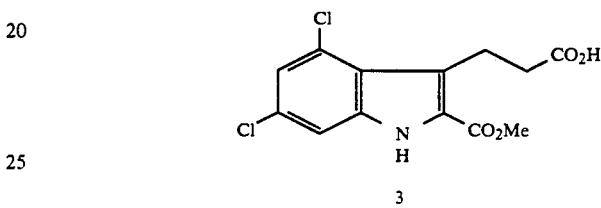

To a solution of the α,β-unsaturated ester 2 (0.95 g, 2.35 mmol) in 40 mL THF is added 10% palladium on charcoal catalyst (0.18 g). The reaction mixture is then stirred at 20° C. for 1 hour. The catalyst was removed by filtration and the residue is washed with ethyl acetate (3×). The filtrate is concentrated and chromatographed by 60% ethyl acetate in hexanes on silica gel to give 0.72 g (97%) of the acid 3 as a pale yellow solid: $^1$H NMR (DMSO-d$_6$, 200 MHz) δ 12.17 (s, 2H), 7.42 (d, 1H, J=1.7 Hz), 7.20 (d, 1H, J=1.7 Hz), 3.90 (s, 3H), 3.50 (dd, 2H, J=8.1, 6.0 Hz), 2.46 (m, 2H, partly buried under the DMSO signal).

EXAMPLE 4

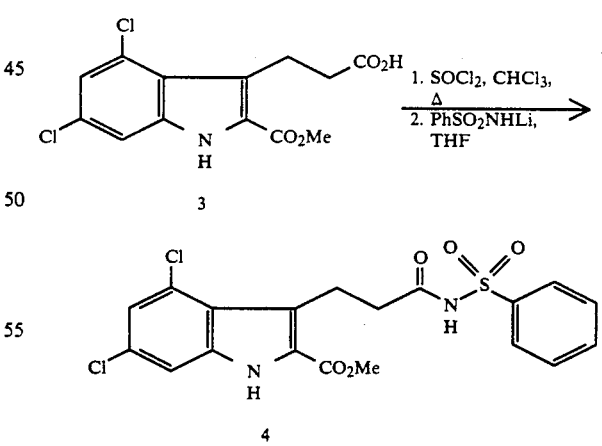

A suspension of the acid 3 (0.72 g, 2.28 mmol) and thionyl chloride (1 mL, 13.7 mmol) in 16 mL of anhydrous chloroform is refluxed for 30 minutes. Excess solvent and thionyl chloride are removed under reduced pressure. The resulting solid is then dissolved in 10 mL of anhydrous THF and the solvent is again removed under reduced pressure to assure complete removal of excess thionyl chloride. The acid chloride is then redissolved in 15 mL of anhydrous THF and set aside. To a solution of benzenesulfonamide (0.75 g, 4.77 mmol) in 30 mL of anhydrous THF at room temperature under argon atmosphere is added 1.6M solution of n-butyllithium in hexanes (2.9 mL, 4.64 mmol). The resulting suspension is allowed to stir at room temperature for 15 minutes and the acid chloride-THF solution is then added quickly. The reaction mixture is allowed to stir at room temperature for 30 minutes. A 0.5N hydrochloric acid solution is added to quench the reaction. The organic layer is separated and the aqueous layer is extracted with ethyl acetate (1×). The combined organic extracts are dried over magnesium sulphate, filtered, and concentrated. The resulting solid is triturated in hot 30% ethyl acetate in hexanes. The suspension is allowed to cool to room temperature and the solid was collected by filtration: $^1$H NMR (DMSO-$d_6$, 200 MHz) δ 12.16 (s, 1H), 12.11 (s, 1H), 7.92 (d, 2H, J=7.36 Hz), 7.67 (m, 3H), 7.40 (d, 1H, J=1.55 Hz), 7.17 (d, 1h, J=1.55 Hz), 3.85 (s, 3H), 3.40 (t, 2H, J=7.26 Hz), 2.5 (m, 2H, partly buried under the DMSO signal).

PREPARATION 4

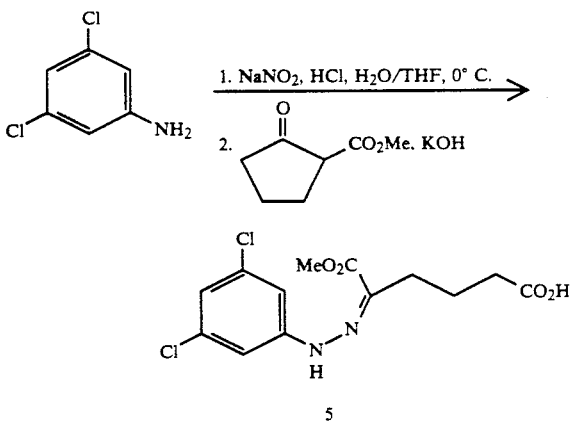

To a solution of concentrated hydrochloric acid (23 mL, 0.28 mol) in 90 mL of water at −5° C. is added a solution of 3,5-dichloroaniline (15.0 g, 93 mmol) in 10 mL THF. The reaction mixture is allowed to stir at −5° C. for 20 minutes and a solution of sodium nitrite (6.4 g, 93 mmol) in 20 mL of water is added slowly. The reaction mixture is kept below 0° C. with stirring until most of the solid went into solution (ca. 30 minutes), the diazonium salt solution is then kept at 0° C. for further use. A potassium hydroxide (16.3 g, 0.29 mol) in 120 mL is prepared and cooled to 0° C. Methyl 2-oxocyclopentanecarboxylate (12.9 g, 91 mmol) is placed in a separatory funnel and was shaken vigorously with 60 mL of the KOH solution. Benzene (15 mL) is then added to extract out the unreacted cyclopentanone. The aqueous layer is collected and the benzene layer is reextracted with the remaining potassium hydroxide solution. The aqueous layers are poured onto 150 g of ice followed by the addition of the diazonium salt solution. The solid formed is collected and dissolved in 500 mL of chloroform. The chloroform solution is washed once with brine and dried with magnesium sulphate. The solid product obtained after filtration and concentration is triturated with ether-hexane mixture. The yellow solid is then collected by filtration and air dried: $^1$H NMR (DMSO-$d_6$, 200 MHz) δ 12.25 (s, 1H), 10.28 (s, 1H), 7.23 (d, 2H, J=1.81 Hz), 7.07 (t, 1H, J=1.81 Hz), 3.76 (s, 3H), 2.59 (t, 2H, J=8.12 Hz), 2.30 (t, 2H, J=7.27 Hz), 1.65 (m, 2H).

PREPARATION 5

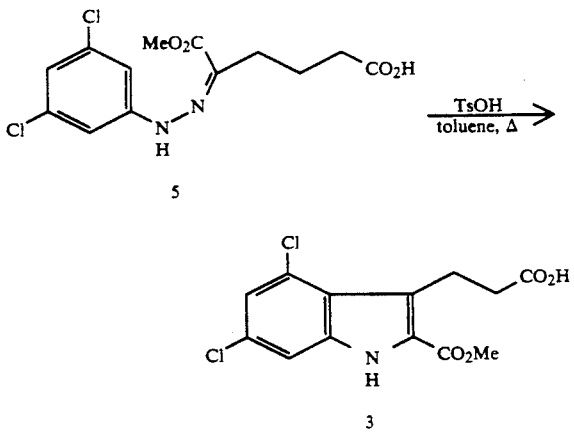

A solution of p-toluenesulfonic acid monohydrate (0.36 g, 1.89 mmol) in 25 mL of toluene is refluxed under azeotropic conditions for 1 hour to remove water. The solution is cooled to room temperature and the hydrazone 5 (0.32 g, 0.95 mmol) is added. The resulting mixture was refluxed for 3 hours and then cooled to 0° C. Saturated sodium carbonate solution (20 mL) and water (10 mL) are added to quench the reaction. The aqueous layer is collected and washed once with ethyl acetate and then cooled to 0° C. followed by acidification with concentrated hydrochloric acid to pH 1. The precipitates are collected by filtration and washed with water (4×). The indole carboxylic acid 3 (0.18 g, 60%) is obtained as an off-white powder after being air-dried overnight: $^1$H NMR (DMSO-$d_6$, 200 MHz) δ 12.17 (s, 2H), 7.42 (d, 1H, J=1.7 Hz), 7.20 (d, 1H, J=1.7 Hz), 3.90 (s, 3H), 3.50 (dd, 2H, J=8.1, 6.0 Hz), 2.46 (m, 2H, partly buried under DMSO signal).

PREPARATION 6

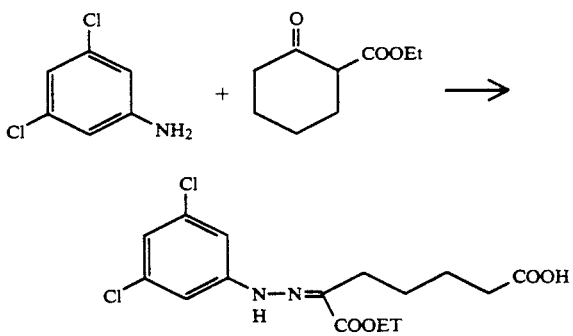

3,5-Dichloroaniline (50.0 g, 0.31 mole) and ethylcyclohexanone-2-carboxylate (52.5 g, 0.31 mole) were reacted in a manner similar to reaction XXX to give 117 g of the hydrazone as a red solid. This was dried in refluxing toluene with a Dean-Stark trap and used directly in the next reaction.

PREPARATION 7

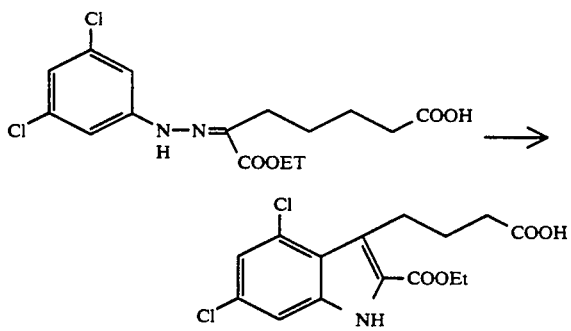

The hydrazone (90 g, 0.26 mole) was cyclized in 500 mL toluene with 49 g toluene sulfonic acid as in the previous example to give 22.7 g, 27%, of a white solid; mp 223°–224° C.

Calc.: C, 52.34; H, 4.39; N, 4.07; Cl, 20.60;
Found: C, 51.97, H, 4.26, N, 3.83, Cl, 20.70.

EXAMPLE 5

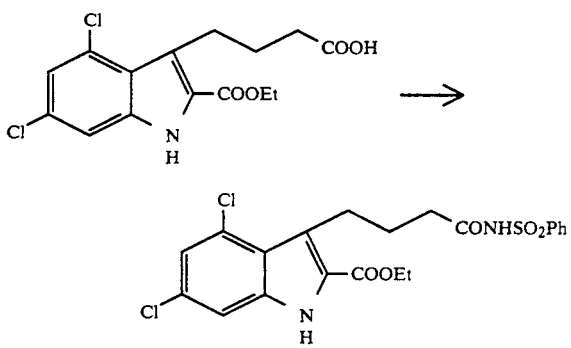

The above indole (1.0 g, 2.9 mmole) was dissolved in 50 mL DMF. CDI (0.94 g, 5.8 mmole) was added and the solution heated at 60° C. under an atmosphere of nitrogen for 2 hours, then the yellow solution cooled to 25° C. Sodium hydride, 60% in oil (0.35 g, 8.7 mmole) was slurried in 25 mL DMF under nitrogen, then benzenesulfonamide (1.4 g, 8.7 mmole) added. The foamy white mixture was stirred for 1 hour then the CDI complex solution was added. After 10 minutes a yellow solution was formed. This solution was stirred for 16 hours at 25° C. then poured onto ice/HCl. The resulting white solid was filtered then dissolved in 200 mL ethyl acetate, washed with water and brine, then dried with sodium sulfate. The yellow liquid was filtered and concentrated to a yellow solid, triturated in ethyl acetate/heptane, washed with heptane, and dried at 100° C. with phosphorus pentoxide in a vacuum. The yield was 950 mg, 68%, of a white solid melting at 200° C.

Calc.: C, 52.18; H, 4.17; N, 5.80; Cl, 14.67;
Found: C, 51.92, H, 4.04; N, 5.36; Cl, 14.51.

EXAMPLE 6

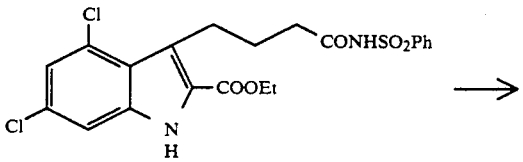

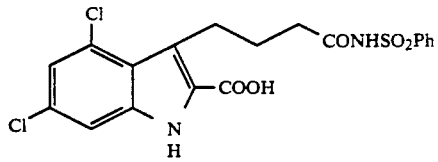

The above ester (400 mg, 0.83 mmole) was stirred with 10 mL THF and 6 mL 1N LiOH for 7 days. The THF was removed, water was added, and the product was precipitated by acidification with 1N HCl, filtered and dried at 110° C. in a vacuum with phosphorus pentoxide.

Calc.: C, 50.12; H, 3.54; N, 6.15; Cl, 15.57;
Found: C, 49.93; H, 3.57; N, 5.86; Cl, 15.74.

EXAMPLE 7

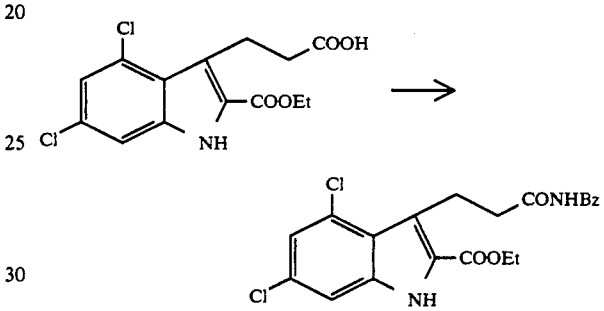

The above indole (2.0 g, 6.3 mmole) was dissolved in 100 mL toluene with diphenylphosphoryl azide (1.9 g, 7.0 mmole) and triethylamine (710 mg, 7.0 mmole). The mixture was stirred at 25° C. for 0.5 hours, refluxed for 0.5 hours, and cooled to 25° C. Benzyl amine (6.74 g, 63 mmole) was added and the slurry refluxed for 2 hours, cooled, and stirred at 25° C. for 16 hours. The reaction was poured into 300 mL water and 200 mL ethyl acetate. The water layer was removed and the organic layer was filtered. The solid was the urea. The filtrate was evaporated, the residue triturated in ethyl acetate/heptane, the solid filtered, and washed with acetone. The ester was used in the next step directly.

EXAMPLE 8

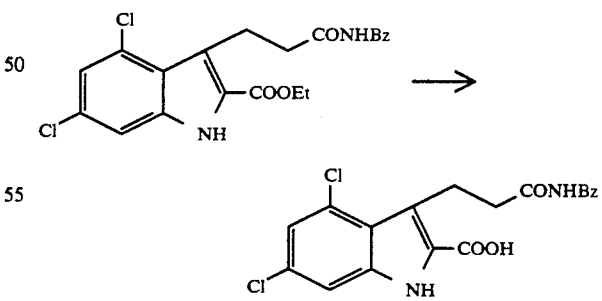

The above ester (180 mg) was dissolved in 10 mL THF and 3 mL 1N LiOH and the resulting solution stirred for 24 hours at 25° C. The THF was removed, the residue diluted with water, the product precipitated by acidification with 1N HCl, filtered, and dried at 100° C. in a vacuum with phosphorus pentoxide. The product was a white solid melting at 202° C., 150 mg, 85%.

EXAMPLE 9

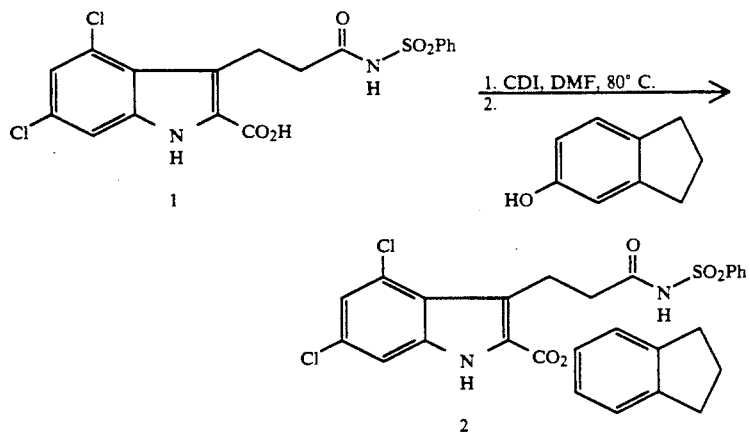

To a solution of CDI in 25 mL anhydrous DMF was added 1 (0.76 g, 1.72 mmol), see Example 4, in one portion. The mixture was allowed to stir at room temperature for 15 minutes, then at 80° C. for 2 hours. The solution was then cooled to room temperature, the 5-indanol added, and stirring continued for 16 hours. The reaction was quenched by pouring into 200 mL H$_2$O, and the resulting yellow precipitate filtered and air dried. Column chromatography (30% EtOAc/Hex→50% EtOAc/Hex) yielded 0.24 g (25%) of 2, mp 258°-260° C.
Calc.: C, 58.18; H, 3.98; N, 5.03;
Found: C, 58.28; H, 3.96; N, 4.73.

EXAMPLE 10

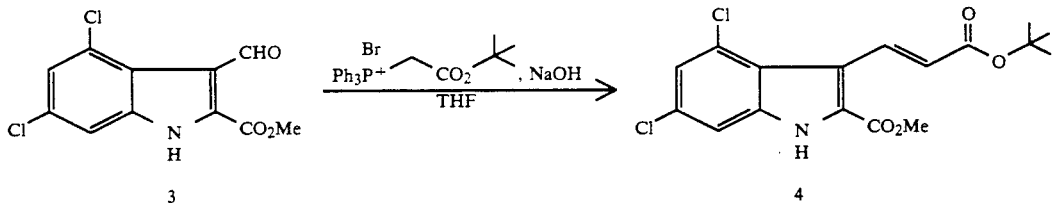

A solution of phosphonium salt (10.54 g, 23.05 mmol) in 75 mL (CH$_2$Cl$_2$) was added to a solution of NaOH (3.14 g, 78.5 mmol) in 125 mL ice water. The reaction was allowed to sit for 10 minutes, then extracted with CH$_2$Cl$_2$. The combined organic layers were dried over MgSO$_4$, filtered, and concentrated to yield an off-white solid. The yield (4.26 g, 11.31 mmol) was then added to a solution of 3 (2.18 g, 8.01 mmol) in 75 mL dry THF, and the mixture allowed to stir at room temperature for 5 hours. The reaction was then concentrated, and the residue chromatographed on SiO$_2$ using 30% EtOAc/Hex yielded 4.06 g (76%) of 4. $^1$H NMR (300 MHz, DMSO-d$_6$) d 12.7 (s,1H), 8.33 (d, 1H, J=15.9 Hz), 7.5 (s,1H), 7.3 (s,1H), 6.55 (d, H, J=16.2 Hz), 3.91 (s,3H).

EXAMPLE 11

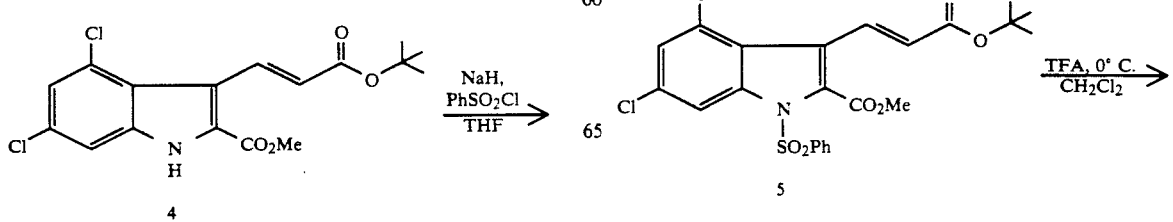

To a solution of indole 4 (3.85 g, 10.4 mmol) in mL of dry THF at 0° C. was added NaH (60% dispersion in mineral oil, 0.98 g, 24.5 mmol). The reaction was stirred at room temperature until H$_2$ evolution ceased. The PhSO$_2$Cl (1.5 mL, 1.75 mmol) was added, and the reaction stirred for 18 hours. The reaction was then cooled to 0° C., quenched with saturated NH$_4$Cl, and extracted with EtOAc. The combined extracts were dried over MgSO$_4$, filtered, and concentrated. $^1$H NMR (300 MHz, DMSO-d$_6$) d 8.26-7.15 (m, 8H), 6.06 (d, 1H, J=15.8 Hz), 3.97 (s, 3H), 1.48 (s, 9H).

EXAMPLE 12

-continued

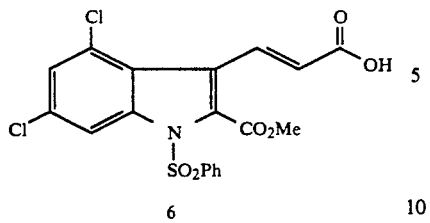

To a solution of ester 5 (5.90 g, 11.56 mmol) in 40 mL of anhydrous CH$_2$Cl$_2$ at 0° C. was added the TFA (10 mL) and the reaction stirred at room temperature for 24 hours. The excess solvent was then removed in vacuo, 50 mL of CCl$_4$ added and then removed. The solid residue was collected by filtration, washed with ether, hexanes, and air dried to yield 4.13 g (79%) of 6. $^1$H NMR (300 MHz, DMSO-d$_6$) d 12.8 (s, 1H), 8.2–7.6 (m, 8H), 6.10 (d, 1H, J=16 Hz), 3.99 (s, 3H).

EXAMPLE 13

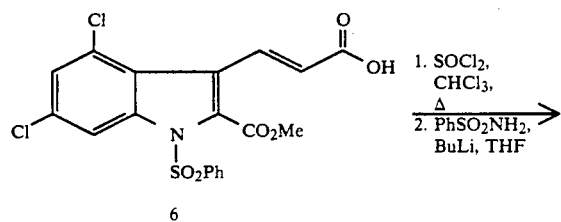

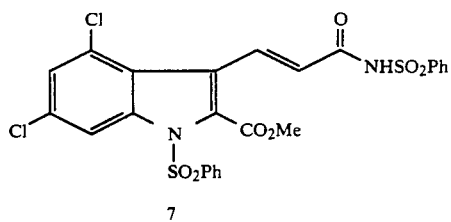

A suspension of acid 6 (0.64 g, 1.41 mmol) and SOCl$_2$ (0.2 mL, 2.74 mmol) in 10 mL of anhydrous CHCl$_3$ was heated to reflux for 1.5 hours. The excess solvent was removed in vacuo, and the solid residue dissolved in 10 mL of anhydrous THF. To a mixture of benzene sulfonamide (0.53 g, 3.37 mmol) in 15 mL of anhydrous THF was added nBuLi (1.6M, 3.52 mmol), and solution stirred at room temperature for 15 minutes, followed by cooling to 0° C. The acid chloride/THF solution was then added to the nBuLi/THF solution, and the reaction stirred for 30 minutes at 0° C. The reaction was quenched with 0.5N HCl, and extracted with EtOAc. The combined organic extracts were washed with NH$_4$Cl solution, dried over MgSO$_4$, filtered, and concentrated. The solid residue was triturated with 50% EtOAc/Hex, filtered, and air dried. Isolate 0.70 g (89%) of 7. $^1$H NMR (300 MHz, DMSO-d$_6$) d 12.65 (s, 1H), 8.2–7.2 (m, 13H), 6.32 (d, 1H, J=15.9 Hz), 4.0 (s, 3H).

EXAMPLE 14

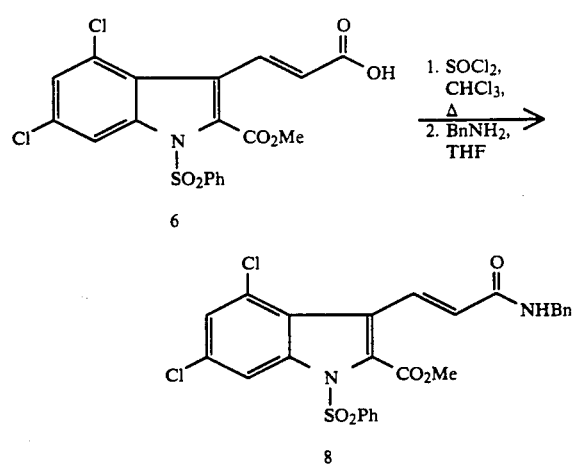

A suspension of acid 6 (0.77 g, 1.70 mmol) and SOCl$_2$ (0.3 mL, 4.11 mmol) in 15 mL of anhydrous CHCl$_3$ was heated to reflux for 2 hours. The excess solvent was removed in vacuo, 10 mL of anhydrous THF added and removed in vacuo. The solid residue was dissolved in 20 mL anhydrous THF and cooled to 0° C. Benzylamine (0.38 mL, 3.48 mmol) was added dropwise, the reaction stirred for 30 minutes at 0° C., quenched with 0.1N HCl, and extracted with EtOAc. The combined extracts were washed with brine, dried over MgSO$_4$, filtered, and concentrated. The pale yellow solid with triturated with 25% EtOAc/Hex, filtered and air dried to yield 0.74 g (80%) of 8. $^1$H NMR (200 MHz, DMSO-d$_6$) d 8.9 (t, 1H, J=5.6 Hz), 8.2–7.2 (m, 13H), 6.38 (d, 1H, J=15.7 Hz), 4.41 (d, 2H, J=5.6 Hz), 4.01 (S, 3H).

EXAMPLE 15

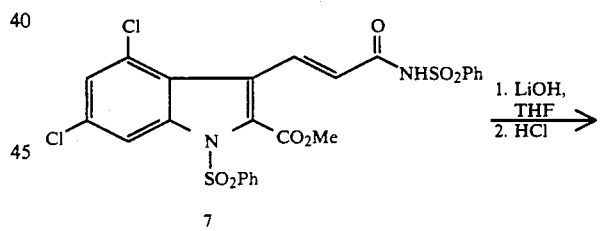

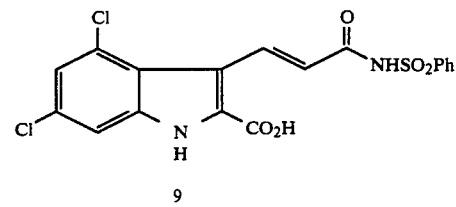

To a solution of ester 7 (0.70 g, 1.18 mmol) in 10 mL of THF at 0° C. was added LiOH (1N, 4mmol), and the reaction stirred at room temperature for 16 hours. The excess solvent was removed, and the residue diluted the 15 mL of water, followed by extraction with ether. The aqueous layer was cooled to 0° C., and acidified with concentrated HCl. The solid product was filtered, washed with water, hexanes, 10% EtOAc/Hex, and air dried to yield 0.36 g (69%) of 9, mp 252°–254° C.

Calc.: C, 49.22; H, 2.75; N, 6.38; Cl, 16.14; S, 7.30; Found: C, 48.85; H, 2.74; N, 6.15; Cl, 15.46; S, 7.14.

EXAMPLE 16

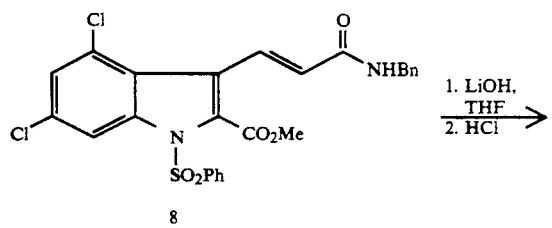

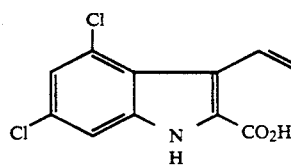

The same procedure used for 9 was followed using 8 (0.74 g, 1.36 mmol) and LiOH (1N, 4 mmol) to yield 0.19 g of 10, mp 245°–247° C.

Calc C, 58.63; H, 3.63; N, 7.20; Cl, 18.22;
Found: C, 58.69; H, 3.66; N, 6.71; Cl, 18.39.

EXAMPLE 17

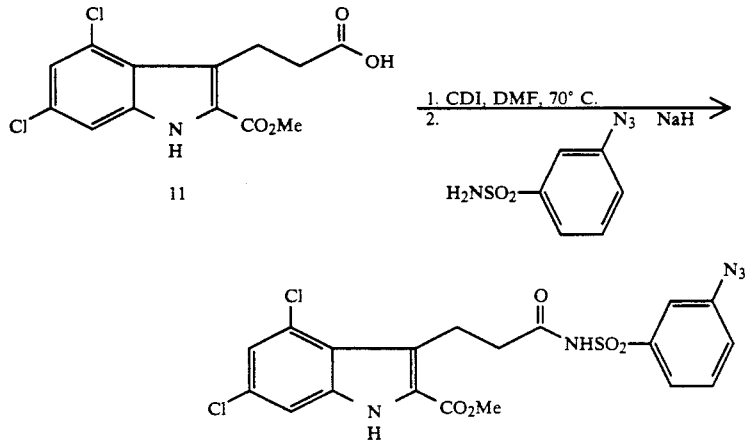

To a solution of 11 (0.99 g, 3.13 mmol) in 30 mL anhydrous DMF was added CDI (1.07 g, 6.6 mmol) and heated to 70° C. for 2 hours. To a second solution of azido sulfonamide (1.88 g, 9.5 mmol) in 40 mL anhydrous DMF, was added NaH (60% dispersion in mineral oil, 0.38 g, 9.5 mmol), and stirred at room temperature for 2 hours. The DMF solution of 11 was added to the second DMF solution, and the entire reaction stirred at room temperature for 16 hours. The reaction was quenched by pouring into 300 mL of ice water with 10 mL concentrated HCl. The solid precipitate was filtered, washed with water, and air dried to yield 1.51 g (97%) of 12. $^1$H NMR (300 MHz, DMSO-$d_6$) d 12.3 (s, 1H), 12.14 (s, 1H), 7.82–6.95 (m, H), 3.85 (s, 3H), 3.40 (m, 2H), (m, 2H).

EXAMPLE 18

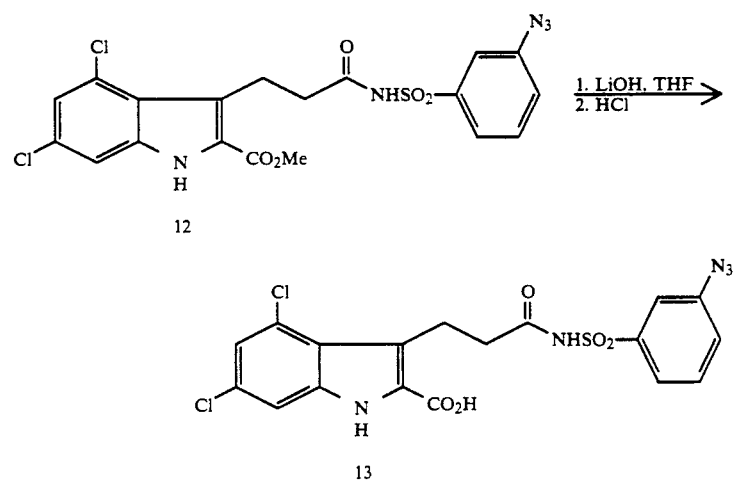

The same procedure for 9 was followed using 12 (0.50 g, 1.01 mmol) and LiOH (1N, 3 mmol) to yield 0.39 g (80%) of 13.

Calc.: C, 44.83; H, 2.72; N, 14.52; Cl, 14.70; S, 6.65;
Found: C, 44.52; H, 2.61; N, 14.26; Cl, 14.83; S, 6.53.

We claim:
1. A compound of the formula

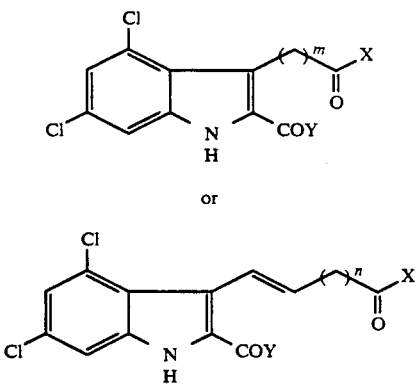

or a pharmaceutically acceptable base or acid addition salt thereof;

wherein m is an integer of one to three and n is an integer of zero or one;

(1) Y is OH; OR$_{30}$ wherein R$_{30}$ is lower alkyl, optionally substituted phenyl, or phenylalkyl wherein the alkyl is an alkylenyl of from one to four carbons and the phenyl is optionally substituted as defined below; NR$_{40}$R$_{50}$ wherein R$_{40}$ and R$_{50}$ are independently hydrogen or lower alkyl; or OCH$_2$OR$_{30}$ wherein R$_{30}$ is as defined above;

(2) X' is OH or X wherein (3) X is NHSO$_2$R$^3$ or NHR$^3$ wherein R$^3$ is (i) hydrogen; (ii) alkyl of from one to twelve carbons; (iii) cycloalkyl or cycloalkyllower-alkyl; (iv) alkenyl of from two to twelve carbons; (v) alkynyl of from two to twelve carbons; (vi) aryl which is phenyl unsubstituted or substituted by one to three of lower alkyl, halogen, trifluoromethyl, nitro, amino, mono- or di-lower alkylamino, azido, hydroxy, lower alkoxy, C(O)OH, or NHCOR$^5$ wherein R$^5$ is lower alkyl, lower alkenyl, aryl, arylloweralkyl, arylloweralkenyl, heteroaryl or heteroloweralkyl, in which heteroaryl is as defined below, NHSO$_2$R$^5$ wherein R$^5$ is as defined above, CN, CONHR$^8$ wherein R$^8$ is hydrogen or lower alkyl, S(O)$_{0-2}$R wherein R is hydrogen or lower alkyl; (vii) aryl-loweralkyl; (viii) arylloweralkenyl; (ix) a heterocycle group selected from the group consisting of tetrahydropyranyl, tetrahydrofuranyl, and tetrahydrothienyl; (x) a heteroaryl selected from the group consisting of thienyl, benzothienyl, furanyl, and benzofuranyl, or (xi) (CH$_2$)$_q$R$^7$ wherein q is an integer of one to four and R$^7$ is (A) heterocycle as defined above, (B) heteroaryl as defined above, (C) SO$_3$R$^8$ wherein R$^8$ is as defined above, (D) PO$_3$R$^8$ wherein R$^8$ is as defined above, (E) CO$_2$R$^8$ wherein R$^8$ is as defined above, or (F) NR$^9$R$^{10}$ wherein R$^9$ and R$^{10}$ are independently hydrogen or alkyl; with the proviso that in a compound of the formula I, X cannot be amino, monoalkylamino, or dialkylamino.

2. A compound according to claim 1 having the Formula II, wherein X' is OH or X, and X is NHSO$_2$CH$_3$, NHSO$_2$phenyl, NHphenyl or NHCH$_2$phenyl.

3. A compound according to claim 1 having the Formula I, wherein X is NHSO$_2$CH$_3$, NHSO$_2$phenyl, NHSO$_2$(CH$_2$)$_4$H, or NHphenyl or NHCH$_2$phenyl or NHSO$_2$phenyl substituted by azido.

4. A compound according to claim 3 and being 4,6-dichloro 3-[3-oxo-3-[(phenylsulfonyl) amino]propyl]-1H-indole-2-carboxylic acid.

5. A compound according to claim 2 and being (E)-3-(2-carboxyethenyl)-4,6-dichloro-1H-indole-2-carboxylic acid.

6. A compound according to claim 3 and being 4,6-dichloro-3-[3-oxo-3-[(methylsulfonyl) amino]propyl]-1H-indole 2-carboxylic acid.

7. A compound according to claim 3 and being 4,6-dichloro-3-[4-oxo-4-[(phenylsulfonyl) amino)butyl]-1H-indole-2-carboxylic acid.

8. A compound according to claim 3 and being 3-[3-[[(3-azidophenyl)sulfonyl]amino]-3-oxopropyl]-4,6-dichloro-1H-indole 2-carboxylic acid.

9. A compound according to claim 2 and being (E)-4,6-dichloro-3-[3-oxo-3-[(phenylsulfonyl) amino]-1-propenyl]-1H indole-2 carboxylic acid.

10. A compound according to claim 2 and being (E)-4,6-dichloro-3-[3-oxo-3-[(phenylmethyl) amino]-1-propenyl]-1H-indole-2-carboxylic acid.

11. A pharmaceutical composition comprising a therapeutically effective amount of a compound of claim 1 together with a pharmaceutically acceptable carrier.

12. A method for treating cerebrovascular disorders which comprises administering to a patient in need thereof the compound of claim 1 in unit dosage form.

13. A method for treating disorders responsive to the blockade of glutamic and aspartic acid receptors which comprises administering to a patient in need thereof the compound of claim 1 in unit dosage form.

14. A method for treating stroke which comprises administering to a patient in need thereof the compound of claim 1 in unit dosage form.

* * * * *

UNITED STATES PATENT AND TRADEMARK OFFICE
CERTIFICATE OF CORRECTION

PATENT NO. : 5,284,862

DATED : February 8, 1994

INVENTOR(S) : Bigge, et al

It is certified that error appears in the above-indentified patent and that said Letters Patent is hereby corrected as shown below:

Column 31, line 12, delete "X" and insert instead "X'".

Signed and Sealed this

Fourteenth Day of June, 1994

Attest:

BRUCE LEHMAN

Attesting Officer     Commissioner of Patents and Trademarks